United States Patent
Oettel et al.

(10) Patent No.: US 6,689,768 B2
(45) Date of Patent: Feb. 10, 2004

(54) PHARMACEUTICAL PREPARATIONS FOR TREATING SIDE EFFECTS DURING AND/ OR AFTER GNRHA THERAPY

(75) Inventors: Mcihael Oettel, Jena (DE); Ludwig Wildt, Herzogenaurach-Haundorf (DE); Peter Licht, Bubenreuth (DE); Joachim Neuwinger, Erlangen (DE); Wolfgang Hummel, Neuenmarkt (DE); Ralph Dittrich, Erlangen (DE)

(73) Assignee: Jenapharm GmbH & Co. KG, Jena (DE)

( * ) Notice: Subject to any disclaimer, the term of this patent is extended or adjusted under 35 U.S.C. 154(b) by 107 days.

(21) Appl. No.: 09/891,722

(22) Filed: Jun. 26, 2001

(65) Prior Publication Data

US 2002/0065260 A1 May 30, 2002

Related U.S. Application Data

(63) Continuation-in-part of application No. 09/291,385, filed on Apr. 14, 1999, now abandoned.
(60) Provisional application No. 60/081,791, filed on Apr. 15, 1998.

(51) Int. Cl.[7] .......................... A61K 31/56; A61K 31/58
(52) U.S. Cl. .................. 514/182; 514/176; 514/182; 552/505; 552/610; 552/613; 552/625; 552/626; 552/627; 552/630
(58) Field of Search ................... 514/176, 182; 552/610, 613, 625, 626, 627, 630

(56) References Cited

U.S. PATENT DOCUMENTS 5,661,143 A * 8/1997 D'Amato et al. ............ 514/182

OTHER PUBLICATIONS

Pribluda et al., Cancer and Metastasis, 19, (2000), 173–179.*

* cited by examiner

Primary Examiner—Sabiha Qazi
(74) Attorney, Agent, or Firm—Michael J. Striker

(57) ABSTRACT

The pharmaceutical preparations for treating side effects, such as hot flashes, prostate enlargement and gynecomastia, during and/or after treatment with analogs or antagonists of gonadotropin-releasing hormone (GnRHa therapy) contain an effective amount of a chemically modified derivative of 17α-estradiol, a chemically modified derivative of 17β-estradiol and/or a chemical modified derivative of estriol. Pharmaceutical preparations containing 14α, 15α-methylene-1,3,5(10),8-tetraene-3,17α-diol are particularly preferred.

9 Claims, 2 Drawing Sheets

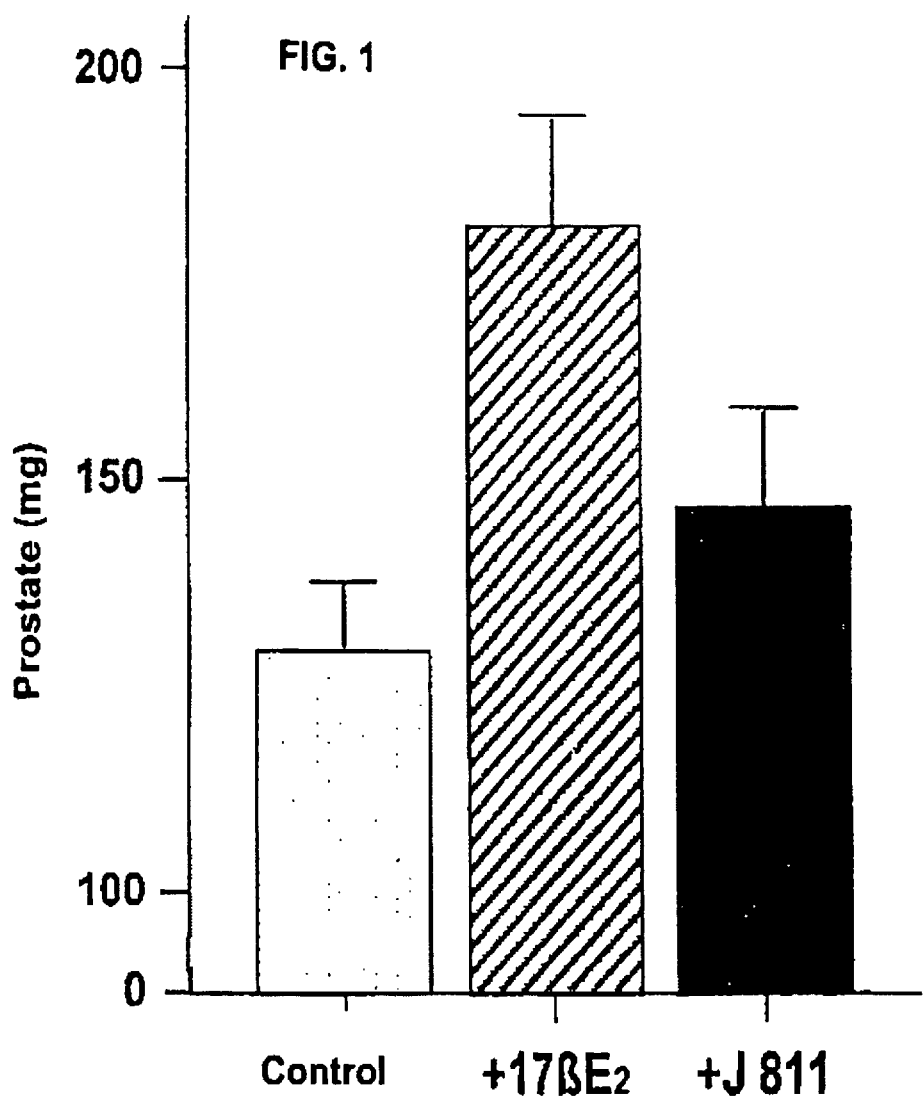

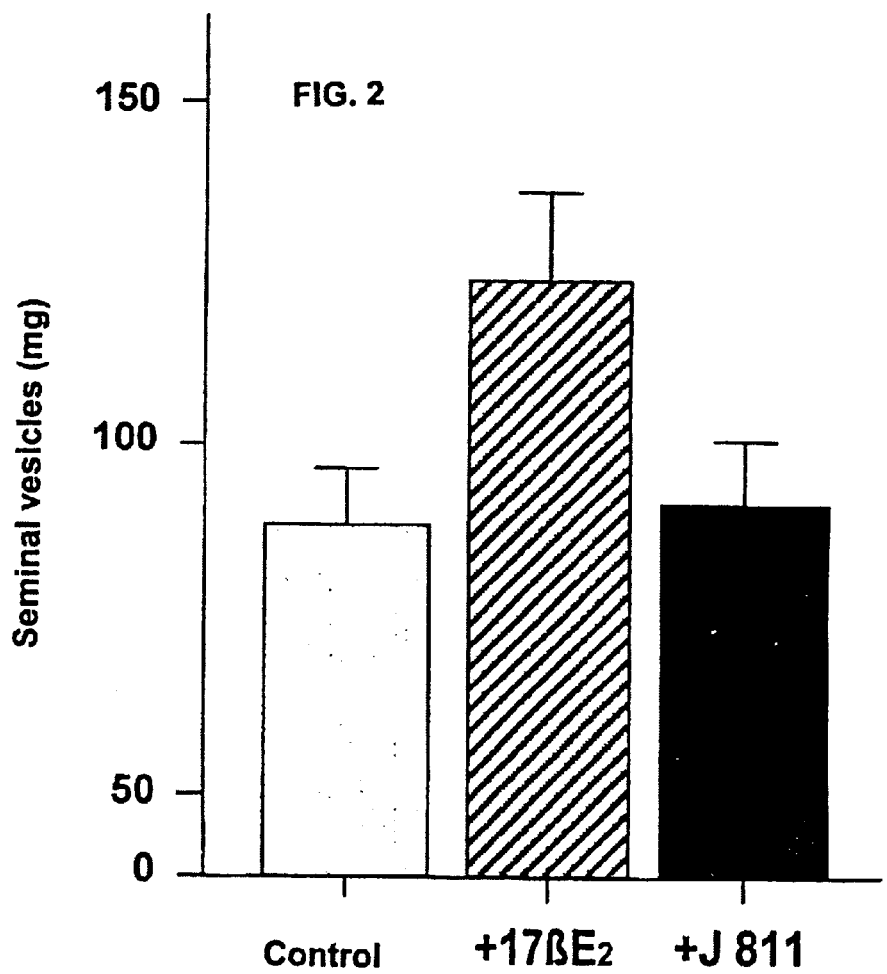

PHARMACEUTICAL PREPARATIONS FOR TREATING SIDE EFFECTS DURING AND/OR AFTER GNRHA THERAPY

CROSS-REFERENCES

This application is a continuation-in-part of U.S. patent application Ser. No. 09/291,385 filed Apr. 14, 1999, now abandoned, which, in turn, claims the benefit of U.S. Provisional Patent Application, Ser. No. 60/081,791, filed Apr. 15, 1998.

BACKGROUND OF THE INVENTION

1. Field of the Invention

The present invention relates to pharmaceutical preparations for reducing the undesirable side effects, such as hot flashes and prostate enlargement, during and/or after treatment with analogs or antagonists of gonadotropin-releasing hormone (GnRHa therapy) in men as well as women. The active ingredients in these pharmaceutical preparations are characterized by estrogen action in the central nervous system. The estrogen side effects in the periphery, e.g. the prostate, the uterus or the breast glands, are reduced or completely eliminated.

2. Related Art

It is known that treatment with analogs or antagonists of gonadotropin-releasing hormone (GnRHa therapy) is an effective therapy in diseases whose intensity is influenced by the activity of the gonads.

Examples of such diseases are endometriosis, benign genital disorders, filbroid tumors of the uterus, endometrial hyperplasia, premenstrual syndrome, catamenial epilepsies, and in the broader sense all cycle-dependent disorders in women, as well as carcinoma of the prostate in men.

According to A. E. Schindler, Der Frauenarzt [The Gynecologist] 2:211–214, 1995, from 8 to 12% of women of reproductive age suffer from endometriosis.

The principal symptoms of endometriosis, along with dysmenorrhea, are dyspareunia as well as cyclical and acyclical pain in the lower abdomen. It is also associated with problems of sterility and infertility.

Now that endometriosis has been identified as a progressive estrogen-dependent disease, attempts have been made to determine, besides surgical correction, what the most effective possible hormone therapy might be. To that end, a regimen for inducing pseudo-pregnancy (W. C. Andrews and G. D. Larsen, Am. J. Obst. Gynecol. 118(5):643–651, 1974), progestational hormones (K. S. Moghissi, J. Obstet. Gynecol. 47:265–267, 1976) and later Danazol (K. W. Schweppe, Endometriose [Endometriosis] 5:4–11) have primarily been employed. Today, GNRH analogs are available for inducing a reversible, medication-induced hypoestrogenism (P. A. Regidor, et al, Zentralbl. Gynädkol. [Central Gynecology Newsletter] 118:283–290, 1996).

The GNRH analogs used, such as Goserelin or Leuprorelin, slow down the development of gonadotropin in the pituitary gland and thus stop estrogen production in the ovaries and lead to amenorrhea, among other effects. They must either be injected once a month or administered twice daily as a nasal spray. The side effects of the GnRH analogs are similar to the complaints that occur during menopause, such as hot flashes, sweating, headaches and depression.

Hot flashes and sweating are among the most unpleasant side effects of GnRHa therapy, which is also used in men for advanced and/or metastatic prostate cancer and thus is widely used. As a treatment that slows down hormonal action, GnRHa therapy is a palliative therapeutic principle. The quality of life of the patient during the treatment is given particular weight. According to S. Kliesch et al, Dtsch. Med. Wschr. [German Medical Weekly] 122:94–945, 1997, the incidence of hot flashes and the attendant outbreaks of sweating is a frequent and undesired accompanying symptom in up to 80% of female patients.

A comparable incidence of hot flashes in men is described as being 58% after orchiectomy and 63% in therapy with GNRH analogs (A. V. Kaisary et al, Brit. J. Urol. 67:502–508, 1991)

To prevent hot flashes in general, until the present moment, for both women and men estrogens are the means of choice. In menopause and post-menopause, they have gained wide use in therapy for menopause-related complaints.

International Patent Disclosure WO 97/21704 discloses novel compounds as GNRH antagonists, among others in combination with estrogens, including therapy for hot flashes.

In GNRH analog therapy, the use of estrogens is not advisable, because the fundamental disease being treated is an estrogen-dependent disease (G. S. Dizerga et al, Fertil. Steril. 33:649–653, 1980) and would aggravate the clinical picture is estrogens were given.

Even in men, with GnRHa therapy for carcinoma of the prostate, the conventional administration of estrogens should be considered with restraint.

The undesired side effects that occur in estrogen therapy are exhibited among other ways in metabolic effects, which for instance lead to an increase in the binding globulins for sexual steroids, thyroid hormones, and cortisone. They are expressed as breast tenderness, headache, fluid retention, nausea, weight gain, and depression (R. Jewelewicz, Fertil. Steril. 67:1–12, 1997).

In men undergoing estrogen therapy, cardiovascular complications can also be expected as an important side effect (R. Haapianen et al, Brit. J. Urol. 66:94–97, 1990; R. Stege et al, Urologie [Urology] 34:398–403, 1995). Feminizing effects are also possible (e.g. gynecomastia).

SUMMARY OF THE INVENTION

The object of the invention is to discover novel pharmaceutical preparations with high effectiveness for treating side effects, such as hot flashes, during and/or after a treatment with analogs or antagonists of gonadotropin-releasing hormone (GnRHa therapy), without the above-mentioned undesirable side effects of the "classical" estrogens occurring.

The pharmaceutical preparations according to the invention for reducing the undesirable side effects, such as hot flashes, during and/or after treatment with analogs or antagonists of gonadotropin-releasing hormone in men as well as women, contain at least one active ingredient selected from the group comprising chemically modified derivatives of 17α-estradiol, chemically modified derivatives of 17β-estradiol or estriol. The discovery of these novel preparations has attained the above set forth object of the invention.

Advantageous embodiments of the pharmaceutical preparations of the invention include the following particular active ingredients:

14α,15α-methylene-1,3,5(10),8-tetraene-3,17α-diol 4-methylestra-1,3,5(10)-triene-1,17α-diol 4-methylestra-1,3,5(10),6-tetraene-1,17α-diol 4-methylestra-1,3,5(10),6,8-pentaene-1,17α-diol ent-estradiol 4-methylestra-1,3,5(10),6-tetraene-1,17β-diol
4-methylestra-1,3,5(10),6,8-pentaene-1,17β-diol
17α-4'-hydroxyphenylmethyl-4-methylestra-1,3,5(10) triene-1,17β-diol
17α-4'-hydroxyphenoxymethyl-4-methylestra-1,3,5(10)-triene-1,17β-diol
17α-4'-hydroxythiophenoxymethyl-4-methylestra-1,3,5(10)-triene-1,17β-diol
17α-4'-dimethylaminophenoxymethyl-4-methylestra-1,3,5(10)-triene-1,17β-diol
17α-4'-dimethylaminophenylmethyl-4-methylestra-1,3,5(10)-triene-1,17β-diol
17α-3',5'-dimethyl-4'-hydroxyphenyl methyl-4-methylestra-1,3,5(10)-triene-1,17β-diol
17α-3',5'-dimethyl-4'-hydroxyphenylmethyl-4-methylestra-1,3,5(10),6-tetraene-1,17β-diol
17α-4'-hydroxyphenoxymethyl-4-methylestra-1,3,5(10),6-tetraene-1,17β-diol
14β,15β-methylene-8-dehydroestradiol
14β,15β-methylene-1,3,5(10),8-tetraene-3,17α-diol
14β,15β-methylene-1,3,5(10),8-tetraene-3,17β-diol
14α,15α-methylene-1,3,5(10),8-tetraene-3,17β-diol
6-dehydroestriol
9(11)-dehydroestriol The pharmaceutical preparations according to the invention include preparations for oral and parenteral administration, including topical, rectal, subcutaneous, intravenous, intramuscular, intraperitoneal, intranasal, intravaginal, intrabuccal, or sublingual administration, which along with typical vehicle and diluent agents include at least one of the active ingredients recited above or in the claims appended hereinbelow.

The forms of the administered preparations according to the invention include those given by mouth, such as tablets, capsules and lozenges or solutions; percutaneous preparations such as transdermal therapeutic systems (TTSS) or gels, sprays or salves; intranasal preparations, such as a nasal spray or nose drops; rectal preparations, such as suppositories, and parenteral preparations, such as implants, pills, and ampoules. The various embodiments of the administrated preparations are prepared with the usual solid or liquid vehicles and diluents and the typically used pharmaceutical industry adjuvants, in accordance with the desired type of administration, in suitable dosages, in the known way. The advantages of the invention are attained essentially because pharmaceutical preparations have been discovered which prevent the conventional side effects, such as hot flashes, prostate reduction and/or gynecomastia, during and/or after a treatment with analogs or antagonists of gonadotropin-releasing hormone (GnRHa therapy) both in women and in men.

The same is true for side effects in other possible hormone-suppressing therapies.

BRIEF DESCRIPTION OF THE DRAWING

The objects, features and advantages of the invention will now be illustrated in more detail with the aid of the following examples, with reference to the accompanying drawing, in which FIG. 1 is a graphical illustration of the effect of administering 17β-estradiol and 14α, 15α-methylene-1,3,5(10),8-tetraene-3,17α-diol, the preferred effective ingredient according to the invention, to the prostate of male rats; and FIG. 2 is a graphical illustration of the effect of administering 17β-estradiol and 14α, 15α-methylene-1,3,5(10),8-tetraene-3,17α-diol, the preferred effective ingredient according to the invention, to the seminal vesicles of male rats.

EXAMPLES

I. Model Study in Male Rats

A model study was performed in which both 17β-estradiol and 14α, 15α-methylene-1,3,5(10),8-tetraene-3,17α-diol were administered to male rats. The purpose of this study was to compare the extent of the undersirable side effects produced in males (in this case male rats as a model) that are produced by administration of an estrogen, namely 17β-estradiol, and by 14α, 15α-methylene-1,3,5(10),8-tetraene-3,17α-diol, an effective ingredient of the present invention.

Respective amounts of 17β-estradiol and 14α, 15α-methylene-1,3,5(10),8-tetraene-3,17α-diol equivalent to 0.04 mg/kg body weight were administered over a 21 day period to the male rats in corresponding groups of male rats. These amounts were administered daily over the 21 day period to individual male rats subcutaneously. Eight male rats were in each group.

The moisture content in the prostate and seminal vesicles of each tested male rat was measured at the end of the 21 day test period. The results for the increase in moisture in the prostate are shown in FIG. 1. The results for the increase in moisture in the seminal vesicles are shown in FIG. 2. The experimental error estimate is shown with the "T" at the top of each bar in the respective bar graphs.

The results shown in FIG. 1 clearly show that there is scarcely any proliferation effect in the prostates of the male rats due to administration of 14α, 15α-methylene-1,3,5(10),8-tetraene-3,17α-diol (J811), while estradiol (17βE$_2$) administration produces a comparatively large proliferation effect, i.e. an increase in the moisture content.

Furthermore the results shown in FIG. 2 clearly show that there is no profileration effect on the seminal vesicles of male rats due to administration of 14α,15α-methylene-1,3,5(10),8-tetraene-3,17α-diol (J811), while estradiol (17βE$_2$) administration produces a comparatively large proliferation effect, i.e. an increase in the moisture content.

In other words, there are no undesirable estrogen side effects due to administration of 14α, 15α-methylene-1,3,5(10),8-tetraene-3,17α-diol, but estrogen side effects of course result when estradiol is administered to male rats.

II. Clinical Study in Human Females

1. Methods

The symptoms displayed were investigated in the context of clinical studies in men as well as women. Here clinical studies in women with endometriosis are reported.

The effectiveness of injected Decapeptyl-Depot (Ferring Arzneimittel GmbH, Kiel, Germany) in a dose of 3.2 mg of Triptorelin intramuscularly at intervals of four weeks and 1 to 2 mg of 14α,15α-methylene-1,3,5(10),8-tetraene-3,17α-diol daily, given in the form of a vaginal suppository of 1 mg of 14α,15α-methylene-1,3,5(10),8-tetraene-3,17α-diol each, was tested in fourteen female test subjects aged 22 to 38, who were being treated with Decapeptyl-Depot for endometriosis for at least six months.

Test subjects aged 22 to 46 with fibroid tumors of the uterus were given the same doses.

The treatment with 14α,15α-methylene-1,3,5(10),8-tetraene-3,17α-diol was begun four weeks after the beginning of GnRHa therapy, that is, at the time of the second Decapeptyl injection.

Hot flashes were recorded by the subjects daily on a control form laid out for a 24-hour day, beginning with the first day of Decapeptyl therapy.

The mean number of hot flashes per 24 hours in weeks 3 and 4 of the GnRHa treatment (that is, before the beginning of the 14α, 15α-methylene-1,3,5(10),8-tetraene-3,17α-diol therapy) was assumed to be 100%, for the sake of better comparability. The number of hot flashes during additional therapy with 14α,15α-methylene-1,3,5(10),8-tetraene-3,17α-diol was indicated as a percentage of the starting value. For five subjects, a measurement of skin temperature over 24 hours was done, for the sake of objectivity.

At intervals of four weeks, immediately prior to the injection of Decapeptyl-Depot, blood was drawn to determine LI-I, FSH, prolactin, testosterone, DHEAS, SHBG, free testosterone, estradiol, and progesterone. Blood specimens were also taken for determining a simple blood count, SGOT, SGPT, creatinine, Na, K, Ca, albumin, glucose and CA 125.

For long-term treatment, bone density was monitored at intervals of 6 to 12 months. In seven subjects, trials of withdrawal from 14α, 15α-methylene-1,3,5(10),8-tetraene-3,17α-diol over 4 to 8 weeks each were done.

2. Results

For all female subjects, hot flashes occurred within four weeks after the onset of GnRHa therapy: on average, thirteen hot flashes per 24 hours; range: 7 to 18. The rise in skin temperature on average was 2.2°.

Within one to three weeks after the first Decapeptyl-Depot injection, bleeding ensued in 10 subjects. In all the subjects, the LH and FSH values dropped below 3 I.U./ml after four weeks. Soon estradiol was on average 20 pg/mi; range: <15 pg/ml to 35 pg/ml. A decrease was found within one week and reached a stable level not later than after three weeks.

No bleeding occurred with the administration of 14α, 15α-methylene-1,3,5(10),8-tetraene-3,17α-diol.

The values for LH, FSH, prolactin, testosterone, DHEAS, SHBG, estradiol, and progesterone remained low and unchanged.

A withdrawal trial led to an increase in hot flashes, within three weeks back to the starting values before the administration of 14α,15α-methylene-1,3,5(10),8-tetraene-3,17α-diol.

No changes in liver values, blood count or electrolytes occurred. There was no change in body weight; for those subjects with borderline RR (n=4, RR around 140/80), the blood pressure dropped to values around 110/70.

The Ca 125 values did not rise.

Endometriosis-specific complaints did not recur during the treatment with 14α,15α-methylene-1,3,5(10),8-tetraene-3,17α-diol.

No intracyclic bleeding occurred.

Over one year, for the four subjects monitored, the bone density did not change significantly.

In subjects with fibroid tumors of the uterus, the uterus size decreased to 40±10% of the starting value within three months. This course of the decrease in uterine volume was identical to the course in subjects who did not receive any 14α,15α-methylene-1,3,5(10),8-tetraene-3,17α-diol.

The supplementary treatment with 14α,15α-methylene-1,3,5(10),8-tetraene-3,17α-diol thus did not influence the effect of the GnRHa therapy on the lower organs.

The results of the study prove that by the administration of the compounds according to the invention, such side effects as hot flashes during and/or after a treatment with analogs or antagonists of gonadotropin-releasing hormone (GnRHa therapy) are avoided or reduced.

The hot flashes tripped by GnRHa therapy in the treatment of endometriosis or fibroid tumors of the uterus were effectively eliminated in the treated females as shown by the above clinical study results. The same result was observed in males with prostate-Ca under GnRHa therapy.

In this respect, all subjects both male and female are complaint-free of complaints that undesirable estrogen-related side effects are occurring as a result of the treatment.

In a withdrawal trial however, hot flashes occurred again after about 2 to 3 weeks.

The acceptance by the subjects of long-term therapy with GNRH analogs for endometriosis and fibroid tumors of the uterus is markedly improved by additionally administering the preparations according to the invention.

While the invention has been illustrated and described as embodied in pharmaceutical preparations for treating side effects during and/or after GnRHa therapy, it is not intended to be limited to the details shown, since various modifications and changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and is set forth in the following appended claims.

We claim:

1. A method of reducing estrogen side effects resulting from treatment of a human female with analogs or antagonists of gonadotropin-releasing hormone, said method comprising, during, after or during and after said treatment with said analogs or said antagonists of said gonadotropin-releasing hormone, administering to said human female an effective amount of 14α, 15α-methylene-1,3,5(10), 8-tetraene-3, 17α-diol, said effective amount being effective to reduce said estrogen side effects resulting from said treatment with said analogs or said antagonists.

2. The method as defined in claim 1, wherein said estrogen side effects are hot flashes.

3. A method of reducing estrogen side effects resulting from treatment of a human male with analogs or antagonists of gonadotropin-releasing hormone, said method comprising, during, after or during and after said treatment with said analogs or said antagonists of said gonadotropin-releasing hormone, administering to said human male an effective amount of 14α, 15α-methylene-1,3,5(10), 8-tetraene-3, 17α-diol, said effective amount being effective to reduce said estrogen side effects resulting from said treatment with said analogs or said antagonists.

4. The method as defined in claim 3, wherein said estrogen side effects consist of at least one of prostate enlargement and gynecomastia.

5. A pharmaceutical preparation for reducing estrogen side effects resulting from treatment of a human male or female with analogs or antagonists of gonadotropin-releasing hormone, said pharmaceutical preparation comprising an effective amount of said 14α, 15α-methylene-1,3,5(10), 8-tetraene-3, 17α-diol, said effective amount being effective to reduce said estrogen side effects resulting from said treatment with said analogs or said antagonists, in a solid or liquid vehicle with at least one diluent or adjuvant.

6. A method of reducing hot flashes triggered by a GnRHa therapeutic treatment of a human female, said method comprising, during, after or during and after said GnRHa therapeutic treatment, administering to said human female an effective amount of 14α, 15α-methylene-1, 3, 5(10), 8-tetraene-3, 17α-diol, said effective amount being effective to reduce said hot flashes triggered by said GnHRa therapeutic treatment.

7. The method as defined in claim 6, wherein said GnRHa therapeutic treatment comprises administering triptorelin to said human female to treat endometriosis.

8. A pharmaceutical preparation for treating side effects during and/or after a treatment with analogs or antagonists of gonadotropin-releasing hormone, said pharmaceutical preparation containing an effective amount, sufficient for treating said side effects, of at least one active ingredient selected from the group consisting of 14α, 15α-methylene-1,3,5(10),8-tetraene-3, 17α-diol, 6-dehydroestriol and 9(11)-dehydroestriol.

9. The preparation as defined in claim 6, wherein said side effects are hot flashes, prostate enlargement or gynecomastia.

* * * * *